(12) United States Patent
Towler et al.

(10) Patent No.: US 6,824,555 B1
(45) Date of Patent: Nov. 30, 2004

(54) COMBUSTION NEEDLE FOR MEDICAL APPLICATIONS

(75) Inventors: Gavin P. Towler, Barrington, IL (US); Anil R. Oroskar, Oakbrook, IL (US); Kurt M. Vanden Bussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 175 days.

(21) Appl. No.: 10/200,794

(22) Filed: Jul. 22, 2002

(51) Int. Cl.[7] .................................................. A61F 7/00
(52) U.S. Cl. ...................... 607/96; 128/898; 606/27; 607/113
(58) Field of Search .................. 607/96–114; 606/27–31

(56) References Cited

U.S. PATENT DOCUMENTS

| | | | |
|---|---|---|---|
| 4,290,435 A | 9/1981 | Waggott | 128/800 |
| 4,679,561 A | 7/1987 | Doss | 128/422 |
| 4,737,628 A | 4/1988 | Lovoi | 250/226 |
| 4,872,458 A | 10/1989 | Kanehira et al. | 128/401 |
| 5,000,920 A | * 3/1991 | Heckmann et al. | 422/60 |
| 5,186,181 A | 2/1993 | Franconi et al. | 128/804 |
| 5,251,645 A | 10/1993 | Fenn | 607/154 |
| 5,354,258 A | 10/1994 | Dory | 601/3 |
| 5,528,561 A | 6/1996 | Castanis | 368/93 |
| 5,707,401 A | 1/1998 | Talmore | 607/88 |
| 5,776,175 A | 7/1998 | Eckhouse et al. | 607/100 |
| 6,275,738 B1 | 8/2001 | Kasevich et al. | 607/101 |
| 6,337,998 B1 | 1/2002 | Behl et al. | 607/101 |
| 6,379,347 B1 | 4/2002 | Maki et al. | 606/17 |

* cited by examiner

*Primary Examiner*—Roy D. Gibson
*Assistant Examiner*—Henry M Johnson, III
(74) *Attorney, Agent, or Firm*—John G. Tolomei; Frank S. Molinaro; Arthur E. Gooding

(57) ABSTRACT

A device is disclosed for generating a high intensity localized heat. The device comprises a conduit defining a channel with a catalyst disposed near the end of the channel. The channel carries a gaseous mixture to the catalyst where the mixture reacts in the presence of the catalyst and generates heat.

50 Claims, 3 Drawing Sheets

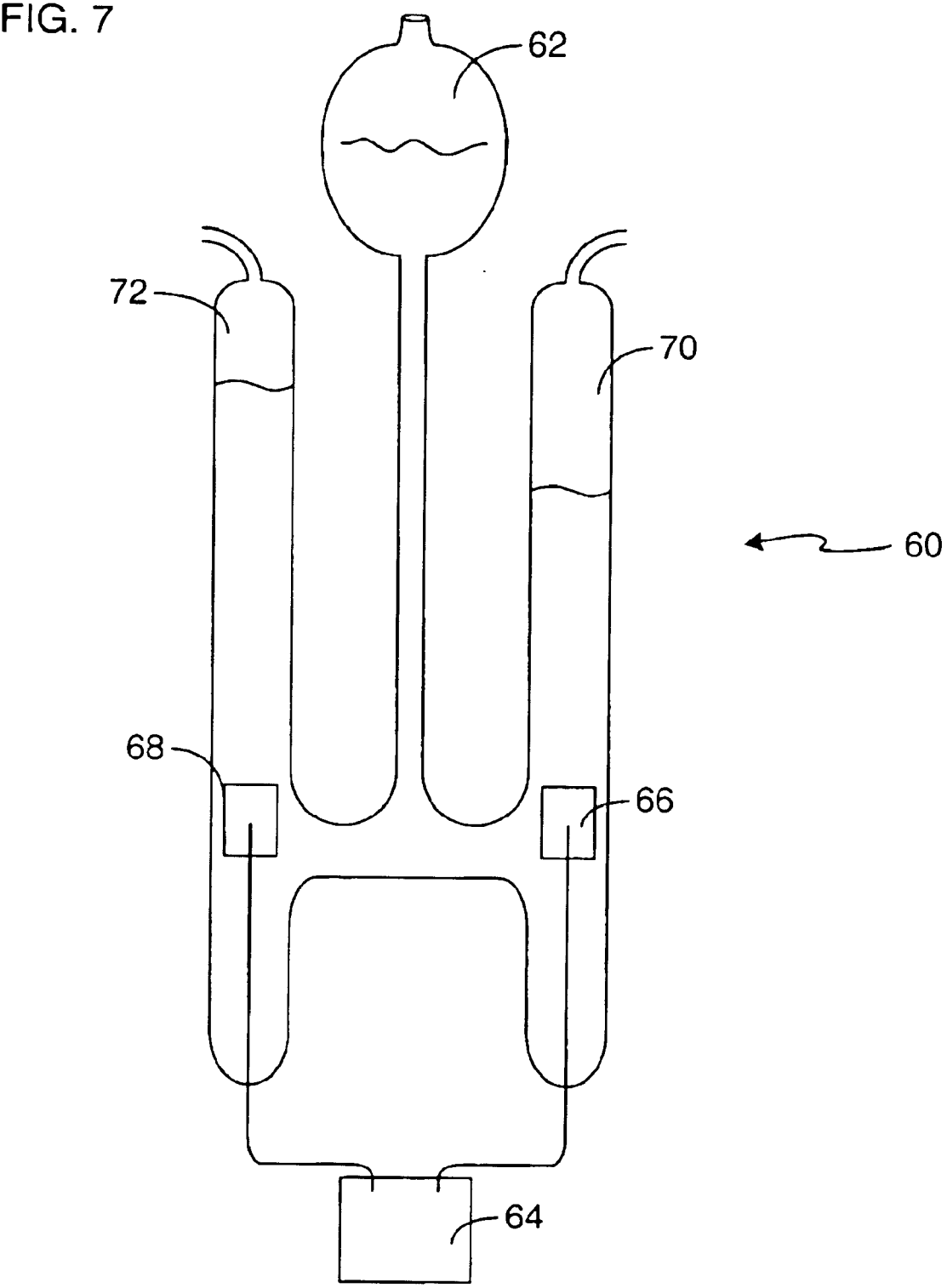

COMBUSTION NEEDLE FOR MEDICAL APPLICATIONS

FIELD OF THE INVENTION

The present invention relates to a device for delivering intense heat to tissue inside the body of a patient for medical applications.

BACKGROUND OF THE INVENTION

Several medical applications require the delivery of high local doses of heat. For example, tumors, warts, and other non-desired tissue growths can be treated by the application of heat to a localized site of the tissue growth. Sufficient application of heat will cause the death of cells near the localized site of heat release. Typically, the temperature necessary to kill tumor cells is in the range of about 43° C. to about 47° C., while at the same time the temperature of normal tissue should be kept below about 43° C.

Localized heat release, or generation, has been achieved by several means. Current approaches for heating tissue include: gamma radiation, lasers, ultrasound, microwave, radio frequency waves, resistance heating, and hot water heating.

One such gamma radiation system is sold under the name GAMMA KNIFE (Elekta Instruments S.A.) and another gamma radiation system is described in U.S. Pat. No. 5,528,561. Multiple beams of ionizing radiation are directed through a patient. The individual beams of ionizing radiation are reduced to minimize the damage to healthy tissue through which the radiation passes while providing a high dosage of radiation to a target region of tissue. The multiple beams are focused and provide a higher dose of radiation at the point of intersection of the multiple beams. Another method involves moving one or more beams of radiation, so that the beams pass through healthy tissue a limited number of times, while passing through the target tissue repeatedly.

Devices for treatment with lasers or photodynamic methods are described in U.S. Pat. Nos. 5,707,401; 6,379,347; 4,737,628 and 4,872,458. The lasers are used to heat the target tissue to a temperature that destroys the target tissue. In some cases, such as for external target tissue, i.e., skin, the tissue is heated until it vaporizes. In order to use the laser to heat the target tissue within the body, the laser requires a guide tube that is generally heat resistant, so as not to heat healthy tissue surrounding the guide tube as the guide tube enters a patient's body.

Ultrasound methods are described in U.S. Pat. No. 5,354,258. While ultrasound can be used, ultrasound also heats up surrounding tissue in the process of heating up target tissue within a patient's body.

Microwave devices have been developed for hyperthermia treatment. One such device is described in U.S. Pat. No. 6,275,738, and treatment is achieved by positioning a radiating antenna system within the tissue to radiate electromagnetic energy into the tissue to be heated. There is a plurality of antenna elements for receiving and reflecting the radiated electromagnetic energy, which involves subjecting the tissue to electromagnetic fields and some heating of the surrounding tissue.

Another method using electromagnetic radiation is treatment with radio frequencies, and descriptions are found in U.S. Pat. Nos. 4,290,435; 5,186,181; 6,337,998; 5,251,645; and 4,679,561. These methods use radio frequencies or other high frequency radiation methods to heat a volume of tissue located within a patient. The tissue is heated by passing high frequency electromagnetic radiation through tissue positioned between two external electrodes located near or in contact with the patient's skin.

Another method for hyperthermia treatment is the use of pulsed electromagnetic radiation, as described in U.S. Pat. No. 5,776,175. This method includes providing a pulsed radiation output from a radiation source and directing the pulsed radiation output toward a tumor.

A significant drawback to each of these methods is subjecting the body to strong electromagnetic fields and often the surrounding tissue is subjected to the radiation, but in lower doses.

Micro-combustion can be used to provide direct heat transfer for local hyperthermia. The use of direct heat transfer overcomes limitations of other methods of hyperthermia treatments by providing a higher heat flux, enhanced localized heat release by fluid exchange, and reduced thermal damage to tissue surrounding a target region.

SUMMARY OF THE INVENTION

The present invention provides a device for generating high intensity localized heat. The system includes a conduit having a supply end and a delivery end, and a catalyst located in proximity to the delivery end. This invention provides a device for generating and controlling an exothermic chemical reaction, and can be termed "a combustion needle".

In one embodiment, the invention further includes a mixing unit. The mixing unit mixes the reactant gases for delivery of a mixture to the supply end of the conduit. The mixing unit provides for a well-mixed gas composition to provide a substantially complete reaction of the mixture.

In one embodiment, the invention further includes an electrolyzer. The electrolyzer provides stoichiometric amounts of gas for mixing in the mixer. The electrolyzer further provides rapid and precise control over the delivery of reactants to the mixer and subsequent rapid and precise control over the generation of heat with the combustion needle.

Other objects, advantages and applications of the present invention will become apparent to those skilled in the art from the following detailed description.

BRIEF DESCRIPTION OF THE DRAWINGS

The description herein makes reference to the accompanying drawing wherein like reference numerals refer to like parts throughout the several views and wherein:

FIG. 7 is a diagram of an electrolyzer.

DETAILED DESCRIPTION OF THE INVENTION

Figure 1:
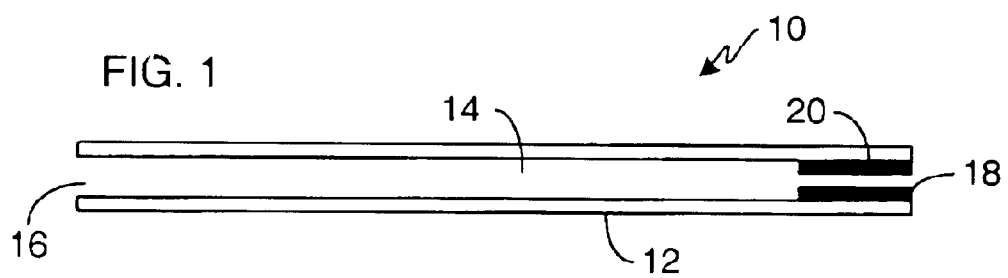
FIG. 1 is an embodiment of a conduit of the present invention.

Several medical applications require the delivery of a high dose of heat to a localized region, or target, of tissue. While other techniques require expensive equipment, the present invention is inexpensive, and provides convenient and safe control over the amount of heat delivered to a small region, or a point source. The purpose is to deliver a dose of heat to kill a small group of cells. The present invention provides that capability at a low cost with precise control over the amount of heat delivered. An advantage of this invention is that all the heat generated is distributed into the target tissue, and the device for delivering the heat into the target tissue is disposable. The generation of the heat is at the target tissue, and there is no waste heat generated and lost in the delivery of heat to the target tissue.

The present invention is a conduit, having a supply end and a delivery end, with openings at both the supply end and the delivery end. The conduit has an inner surface and an outer surface, wherein the inner surface defines a channel. This conduit can be embodied as a narrow, hollow, flexible tube, or needle, having a supply end and a delivery end, wherein the delivery end is the tip of the needle. A catalyst is disposed in proximity to the delivery end of the conduit, or is disposed in proximity to the tip of the needle. Preferably, the catalyst is disposed on the inner surface of the conduit in proximity to the delivery end. The conduit provides a delivery means for delivering well mixed gaseous reactants to the catalyst. The reactants react in the presence of the catalyst and generate heat. The heat generated heats up the delivery end and the surrounding tissue. There is no excess heat generated and lost along the length of the tube as the heat is generated at the site of the catalyst. The amount of heat delivered is controlled by the rate of delivery of reactants to the catalyst. The conduit is sized to provide a stable environment with respect to combustion and ignition, such that upon ignition of the reaction at the delivery end in the presence of the catalyst, the reaction does not propagate up the length of the conduit. That is, the reaction front propagation is insufficient to overcome the rate of delivery of the reactants to the catalyst, and the reaction front is quenched if the reaction products propagate upstream within the conduit to limit reactants reaching the catalyst. For purposes of this application, the term "tube", or "tubular shaped", refers to any conduit capable of carrying the gas. This includes non-circular cross-sectioned conduits, such as conduits having elliptical cross-sections, rectangular cross-sections, or any other cross-sectioned shape capable of defining a conduit.

For medical applications, the preferred reactants are hydrogen and oxygen. The hydrogen and oxygen are delivered in stoichiometric ratios such that when reacted generate water, without excess gases or other waste products. The water generated is in small quantities and is readily absorbed by body tissues. When using hydrogen and oxygen, it has been shown that such a mixture can be formed and is stable with respect to combustion and ignition, provided the channel diameter is less than 400 micrometers.

For non-medical applications, other reactants for generating heat, include acetylene, methane, and other hydrocarbon gases that react with an oxidizing agent. Examples of oxidizing agents include air and oxygen. In the description which follows, hydrogen and oxygen will be used as examples of reactants, but it is understood that the invention is not limited to those reactants.

The channel design can encompass a variety of embodiments. FIG. 1 is a first embodiment of the invention 10, wherein a tubular wall 12 forms a channel 14 having a supply end 16 and a delivery end 18. A catalyst 20 is disposed in proximity with the delivery end 18. The catalyst 20 is any suitable material that facilitates the reaction of a mixture of hydrogen with oxygen to form water. Materials suitable for the catalyst include, but are not limited to, scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), germanium (Ge), indium (In), thallium (Tl), tin (Sn), lead (Pb), antimony (Sb), bismuth (Bi), polonium (Po), and mixtures thereof. The use of a metal for the catalyst is intended to cover oxides of metals, and other metal compounds such as metal sulfates, in addition to the metal in a zero valence state. The oxides of metals includes oxides of Group I and II. Examples of Group I and II metals include sodium (Na), potassium (K), magnesium (Mg), and calcium (Ca). In an alternate embodiment, the choice of catalyst is selected from the group including platinum, palladium, rhenium, rhodium, nickel, iron and mixtures thereof. The deposition of the catalyst 20 is not limited to the inside of the channel 14, but includes the alternate locations of being located on the opening of the delivery end 18, or in proximity to the opening at the delivery end 18 on the exterior of the tubular wall 12.

Figure 2:
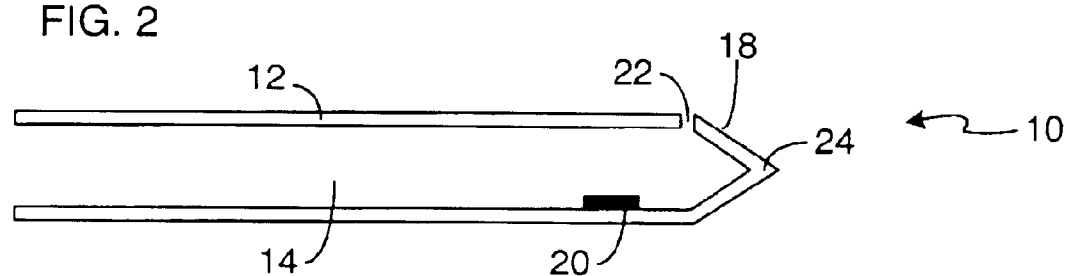
FIG. 2 is an alternate embodiment of the present invention.
Figure 3:
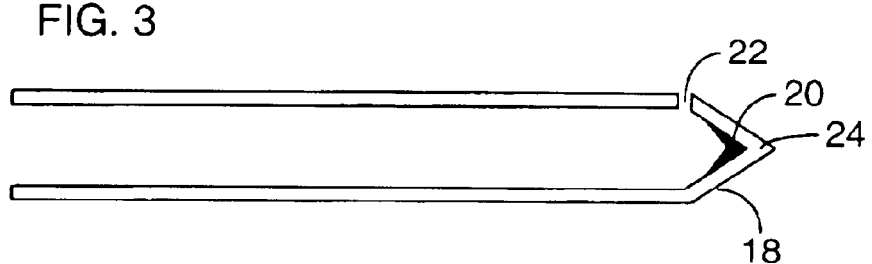
FIG. 3 is an alternate embodiment of the present invention.

An alternate embodiment of the invention 10, as shown in FIG. 2, includes a tubular wall 12 forming a channel 14 with the delivery end 18 having a side opening 22 and a tip 24. The catalyst 20 is disposed on the inside of the tubular wall 12 for delivering heat over a length of the channel 14. In an alternative embodiment, the catalyst is disposed within the tip 24, as shown in FIG. 3. Variations in the invention design include, but are not limited to, a hollow sharp tip, a filled sharp tip, a rounded tip, multiple exit ports in proximity to the tip, side exit ports in proximity to the tip, exit slots, a porous tip, an open tip, and a relatively large single side port. An example of a porous tip includes an end-fritted exit at the tip.

In each variation of the invention, the catalyst is positioned in proximity to an exit port at the delivery end of the conduit. The catalyst can be disposed on the inside of the channel in proximity to the delivery end, within and around any exit ports at the delivery end, on the exterior of the channel in proximity to any exit ports at the delivery end, or in some combination thereof. In one embodiment, the catalyst is disposed on the inside wall of the channel in close proximity to the delivery end.

As an alternative to an open ended conduit with a catalyst in proximity to the delivery end, one embodiment includes a hollow needle having a porous tip at the delivery end, and a catalyst disposed within the porous tip. The gas mixture reacts in the porous tip heating the delivery end. The porous tip can be any porous material that allows sufficient flow with a minimal pressure drop. Examples of porous materials at the end of the conduit include frits, membranes, and screens.

Figure 4:
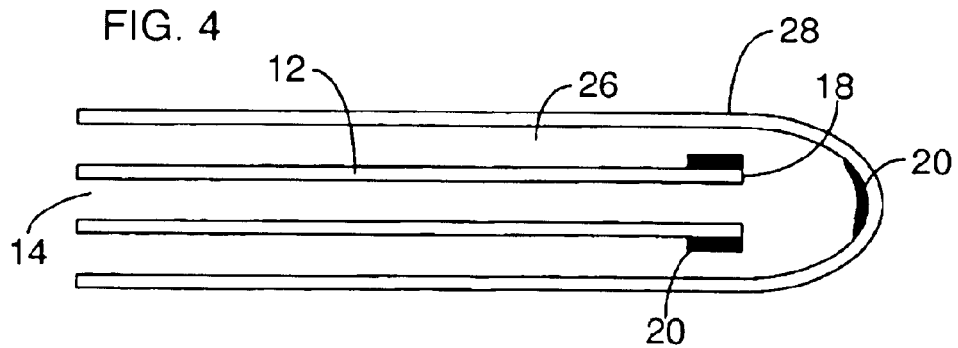
FIG. 4 is an alternate embodiment of the present invention.

In one embodiment, the invention includes a multichannel tubular arrangement as shown in FIG. 4. The invention 10 in this embodiment, can be described as a well 28, with an inserted conduit 12. The well 28 is preferably cylindrical in shape, but may be other geometric shapes. For example, the cross-section may be in the shape of an oval, square, a polygon, D-shaped, segment- or pie-shaped, or the like. The well 28 has a top end, sides, and a closed end e. The top end is open and the bottom end e is permanently closed. The top end may include a flange (not shown), for retaining a seal, such as an O-ring, or for facilitating attachment to an external device. The top end may also include a support structure for holding an inserted conduit 12. The inserted conduit 12 forms an interior channel 14 for carrying gaseous reactants to a catalyst 20. The catalyst 20 is disposed in proximity to the delivery end 18 of the conduit 12. The interior conduit 12 is inserted into the well 28 such that the delivery end 18 is in proximity to the closed bottom end 30 of the well 28. With the proximity of the delivery end 18 of the conduit 12 to the bottom end 30 of the well 28, an optional disposition of the catalyst is an inside surface of the well 28 proximate to the bottom end 30. Optionally, the inserted conduit 12 can be a plurality of smaller conduits 12. With the insertion of the conduit 12 into the well 28, an outer channel 26 is formed between the conduit 12 and the well 28. The outer channel 26 provides a path for removal of products of the reaction. This provides the flexibility to use reactants wherein it is desired to remove the products of the reaction from the target region. For example, the use of a combustible gas wherein at least one of the products of the reaction does not condense and the product gas must be vented, such as carbon dioxide. In this embodiment, the conduit 12 does not need to be concentric with the well 28, and therefore the conduit 12 can be off-centered with respect to the well 28. A variation (not shown) on this embodiment is two substantially parallel tubes, a conduit 12 and an exit tube, connected by a U-shaped tubular member. The U-shaped member connects the delivery end 18 of the conduit 12 to the substantially parallel exit tube for the removal of reaction products through the exit tube.

The conduit design includes a limit on the diameter of the channel 14. The channel is of a diameter sized to provide a stable environment for the mixture of reactants against ignition and combustion in the absence of the catalyst. In a particular embodiment, the conduit inner diameter is sized to provide a stable environment for a mixture of hydrogen and oxygen against ignition and combustion in the absence of the catalyst. The conduit inner diameter is less than 500 micrometers, with a preferred diameter of less than 300 micrometers. A most preferred diameter, balancing the delivery of the reactants with safety and construction of the channel, is a diameter of about 200 micrometers.

The conduit wall, or tube, is made of any suitable material that is substantially impermeable to hydrogen and oxygen. Preferably, the material is flexible to allow for bending of the conduit, such that the conduit may be directed easily within the body of a patient. An additional property of the conduit wall material is for the conduit wall to be constructed in a manner sufficiently rigid such that upon bending of the conduit, no collapse of the channel occurs, i.e., there is no kinking. This is necessary to prevent blocking of the flow of gas within the channel. The amount of bending of the conduit, and therefore the material of choice for the conduit wall, will depend on the specific application. For example, when delivering heat to a tumor or other growth on or just beneath the skin of a patient, bending is unimportant and a rigid stainless steel tube will suffice. In another example, the insertion of the conduit into an artery or vein, for travel along the artery or vein will require a more flexible material, and a suitable material might be a plastic such as high density polyethylene. Suitable materials for the conduit wall include, but are not limited to, stainless steels, inconels, brasses, bronzes, ceramics, thermoplastics, and layered materials that are impermeable to hydrogen and oxygen. An alternative material is a sterile plastic, processed with a thin layer of a material impermeable to hydrogen and oxygen, and having inert properties relative to the hydrogen and oxygen. An example is a plastic tube having a liner of a polyfluorinated hydrocarbon polymer, such as polytetrafluoroethylene (PTFE) also known as TEFLON™, or a TEFLON related polymer. It is also envisioned that this invention includes the possibility of a conduit comprised of a material which acts as a catalyst to the reactants. The conduit in this embodiment is lined with an impervious and unreactive material covering the length of the conduit, except for a measured amount proximate to the discharge end of the conduit. The reactants would therefore only react at the measured amount of conduit exposed to the reactants near the discharge end.

The length of the tube is not critical to the design. The flow of a gas mixture, such as hydrogen and oxygen, will have a very low pressure drop for a tube and is readily overcome by the pressure of the gas mixture leaving the mixer. One embodiment of the invention provides for a channel length of about 0.5 to about 3 meters.

In an alternate embodiment, the invention comprises a multiple conduit array. One such embodiment includes a tube bundle providing multiple conduits each having an inner diameter of less than 400 micrometers, and each conduit terminating at substantially the same position. Each channel supplies reactants to a catalyst in proximity to the delivery end of each conduit, and each conduit delivery end therefore contributes to the delivery of heat to a target tissue region. A variation on this alternative embodiment includes a conduit including a plurality of capillaries within the conduit. An example is described in U.S. Pat. No. 6,357,484 issued on Mar. 19, 2002, which is incorporated by reference in its entirety.

Figure 5:
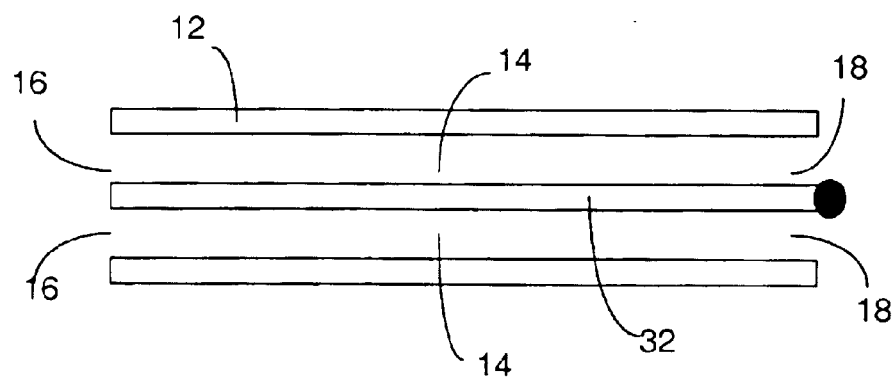
FIG. 5 is an embodiment of the present invention having a conduit with two channels.

In an alternate embodiment, as shown in FIG. 5, the invention comprises at least one conduit, wherein the conduit defines at least two channels 14 and each channel has a supply end 16 and a delivery end 18. The delivery ends 18 of the channels 14 are in proximity to each other, and a catalyst 20 is disposed in proximity to the delivery ends 18. This embodiment has a conduit with an outer wall 12, and an inner wall 32 separating the two channels 14. Optionally, the two channels 14 may be formed of two separate conduits with the delivery ends 18 positioned in proximity to each other. Optionally in this embodiment, a first reactant is carried in one of the at least two channels 14 and a second reactant is carried in the other of the at least two channels 14. The reactants are delivered to the catalyst 20 and mix on exiting the delivery ends 18 of the channels 14 forming a mixture. The mixture reacts on encountering the catalyst 20 disposed in proximity to the delivery ends 18.

The mixer

In one embodiment, the invention further includes a mixing unit, as described in U.S. patent application Ser. No. 09/850,470, filed on May 7, 2001, which is incorporated by reference in its entirety. The mixing unit provides a well mixed gas mixture into the conduit. This allows for larger tubes to feed reactants to the mixer, reducing the overall system pressure drop. The use of the term "tube" is meant to include any structure capable of delivering a fluid along a channel, including ducts having noncircular cross sections.

The mixing apparatus for mixing at least two gaseous reactants, or gaseous fluids, includes a nixing chamber and at least two supply tubes for injecting the fluids into the chamber and arranged about its perimeter. The supply tubes open into the mixing chamber in such a manner that particular fluids introduced at defined flow rates will form a fluid spiral flowing concentrically inward. This vortex formation extends the fluid residence time within the mixing chamber considerably, thereby improving mixing characteristics. Establishment of the desired helical and inward fluid flow path is primarily a function of both the angle of fluid introduction into the mixing chamber and the fluid kinetic energy. Fluids introduced radially, or, in the case of a cylindrical mixing chamber, directly toward its center, will not assume a helical flow path unless acted upon by another fluid with sufficient kinetic energy in the tangential direction. The present mixer achieves exceptional mixing by introducing the first and second fluids to be mixed both tangentially and radially. In one embodiment, the tangential fluid kinetic energy components are adequate to bend the radial flow components so that they assume the overall helical flow pattern with a sufficient number of windings to allow effective mixing. Since one fluid is introduced tangentially and another radially, it is preferred that the ratio of fluid kinetic energy of the tangentially flowing fluid to that of the radially flowing is greater than about 0.5 to provide the desired helical and inward flow pattern.

When proper conditions are established to form the desired helical flow pattern, only that fluid flowing along the outermost winding of the helix contacts the lateral inner surface of the mixing chamber. Depending on the shape and dimensions of the mixing chamber, this fluid accounts for a significant fraction of the pressure drop therein due to frictional losses. Fluid comprising the inner windings, in contrast, is in contact on both sides with rotating fluid only. This fluid comprises previous and subsequent windings flowing in the same direction. For these reasons, the pressure loss achieved with the mixing apparatus of the present invention is lower than that possible for a static mixer using multilamination only and with a correspondingly long mixing path. In this case, the fluids flow as alternating layers in opposite directions. Therefore, frictional effects between adjacent fluid streams flowing along straight or curved pathways are larger. The advantages associated with the use of this apparatus for mixing fluids may therefore be realized in terms of a low pressure loss as well as both a large contact area and long residence time available for diffusive mixing within a small structure.

A further advantage associated with the mixer is the contact between one winding of the fluid spiral or vortex and the previous and subsequent windings, contributing to the diffusive mixing. Preferably, laminar flow conditions prevail from the circular fluid motion in the interior of the mixing chamber. However, it is also possible for localized turbulent flow conditions to result from the overall inward flow of the fluid spiral or vortex.

To form an inward helical flow path, at least one of the supply tubes is arranged to open at an acute angle or tangentially into the mixing chamber. Furthermore, the fluids may be introduced either as their bulk composition entering the mixer or as fluid boundary layers that have been pre-mixed to some extent before entering one or more supply channels. Generally, the tangentially directed fluid maintains laminar flow conditions upon entry into the mixing chamber, in order to form the desired fluid vortex with a multiplicity of windings extending perpendicularly with respect to the plane of the vortex.

The supply tubes may be arranged to open out in one plane around the common mixing chamber. Without regard to the number of supply tubes used, a minimum of two being required, the supply tubes are preferably distributed symmetrically around the circumference of the mixing chamber. These supply tubes can be used to supply the same fluids, for example, Fluid A may be supplied separately in each of supply tubes 50, while Fluid B is supplied in tubes 52. Furthermore, the supply tubes can be arranged in a plurality of planes around the mixing chamber. The same or different fluids can be introduced into the mixing chamber at supply tubes arranged in any given plane. Therefore, fluids may be introduced into a common type of mixing chamber, for example one having a circular cross section in a horizontal plane, through supply tubes at various axial heights about the mixing chamber. Such a design could achieve an even longer fluid spiral, corresponding to longer residence times within the mixing chamber.

The mixing chamber is preferably substantially cylindrical in shape and therefore preferably has a substantially circular cross section. This cross section is advantageously fixed in a substantially horizontal plane from which the mixing chamber outlet leads substantially perpendicularly or in a general vertical direction. Of course, the mixing chamber may have another cross-sectional shape, particularly a rounded form such as an oval or an ellipse. Even forms such as a triangle or other polygons may be acceptable if the corners normally formed at their vertices are rounded. The rounded or curved form prevents dead zones, i.e. regions without a constant flow, that could be problematic if corners or edges are present. In the preferred case of a cylindrically shaped mixing chamber, the height of the supply tubes, at least in the region where they open into the mixing chamber, is preferably less than or equal to the height of the mixing chamber.

The mixing apparatus comprises a mixing chamber outlet that supplies the stream of mixed fluids for downstream applications. In the present invention, the downstream application is the delivery of a gas mixture to a catalyst for combustion of the mixture. The mixing chamber outlet is in fluid communication with, and withdraws mixed fluid from, the central region of the mixing chamber, preferably at its center point. For example, if the mixing chamber is cylindrical and therefore has a circular cross section, the mixing chamber outlet will extract mixed fluid from its center. In one embodiment, the mixing chamber has a substantially circular cross section oriented horizontally and the mixing chamber outlet leads substantially perpendicularly, either upward or downward, therefrom. The cross-sectional area of the outlet compared to that of both the mixing chamber and the cross-sectional areas of the supply tubes opening into it will be set, in view of the specific fluids and their properties, to allow the formation of the desired inwardly flowing fluid vortex with a multiplicity of windings. The resulting mixture is then removed from the center of the fluid vortex. Preferably, the mixing chamber outlet conduit has a circular cross section, as would be the case for a pipe or tube, and the ratio of the diameters of the mixing chamber and mixing chamber outlet is greater than about 5.

As mentioned previously, surprisingly good mixing characteristics are obtained when at least one of the supply tubes provides a substantially tangential injection of fluid into the mixing chamber and at least one also provides a substantially radial injection. It is the tangential fluid motion that imparts a spiral or vortex formation within the chamber. By radial flow is meant a fluid flow directed toward the center of the mixing chamber, whether the chamber is circular, elliptical, or oval. Tangential flow refers to a flow directed at a right angle to this radial flow and generally at or near the surface of the mixing chamber. Substantially tangential or radial flow means that the superior mixing characteristics of the present invention may also be obtained when the flows are not exactly tangentially or radially directed, but are within about 30° of these directions.

In one embodiment, the apparatus comprises not merely two, but a plurality of supply tubes leading alternately substantially tangentially and substantially radially into the mixing chamber. The term "alternately" refers to the tangentially directed supply tubes, designated T, and the radially directed supply tubes, designated R, lying in the order TRTR in at least one plane about the mixing chamber. The supply tubes may also lie alternately in more than one plane; for example, they may be offset in the manner of a chessboard in two dimensions about the circumference and length of the mixing chamber. By varying the positions, in both the horizontal and vertical planes, from which fluids are introduced into the mixing chamber, multiple helical flow paths may be formed, flowing concentrically inward. Thus, for example, a type of double or even triple spiral may be effected. These fluid spirals lie together in one plane and around one center in such a manner that the respective windings lie adjacent to one another.

It is important to note that it is not necessary for entire supply tubes to be oriented in these directions, only those portions in proximate fluid communication with the mixing chamber and impacting the fluid direction into the chamber. For this reason, it is appropriate to refer to the supply tubes as having respective receiving and discharge ends. The receiving ends are in fluid communication with sources of the fluids to be mixed, or feeds, and the discharge ends are in fluid communication with the mixing chamber and are responsible for directing the fluid flow with respect thereto. In one possible design, the supply tubes may be of substantially uniform cross section over their entire length from their receiving end to their discharge end. A substantial change in direction from the receiving end to the discharge end of a supply tube is certainly possible and may even be desired if space about the mixing chamber for multiple tubes is limited. Otherwise, acceleration of the fluid into the mixing chamber, which is often desired to improve mixing, is conveniently accomplished through the narrowing of a supply tube in the direction from its receiving end to its discharge end. Particular design alternatives for supply tubes that narrow in this manner include those having the shapes of funnels, drops, or triangles.

The materials used for construction of the mixer should be sufficiently inert with respect to the process fluids to be mixed. This will help avoid corrosion, erosion, deformation, cracking, or expansion/contraction of the plates, or other detrimental effects potentially resulting from exposure to the fluids under processing conditions. Preferably, inert materials from which the mixer is constructed are selected from the group consisting of polymers (e.g. plastics such as polyvinylchloride or polyethylene), metals, alloys, glass, quartz, ceramic, and semiconductor materials. The same or different materials may be used for the various elements of the present invention, depending on the properties desired at different stages of mixing and/or reaction.

As noted above, the supply tubes may be of uniform cross section or they may narrow in the direction leading to the mixing chamber (i.e. from their respective receiving ends to their discharge ends). Whether the supply tubes narrow or maintain substantially constant cross sectional areas, it is preferred that the ratio of the width of the supply tubes, as measured at their respective points opening into the mixing chamber, to the width of the mixing chamber in the plane of the fluid spiral that forms during operation is advantageously less than or equal to 1:10. Stated otherwise, for a mixing chamber that is substantially cylindrical in shape or otherwise has a substantially circular cross section, the ratio of the diameter of the mixing chamber to the width of each supply channel discharge end is greater than about 10.

Figure 6:
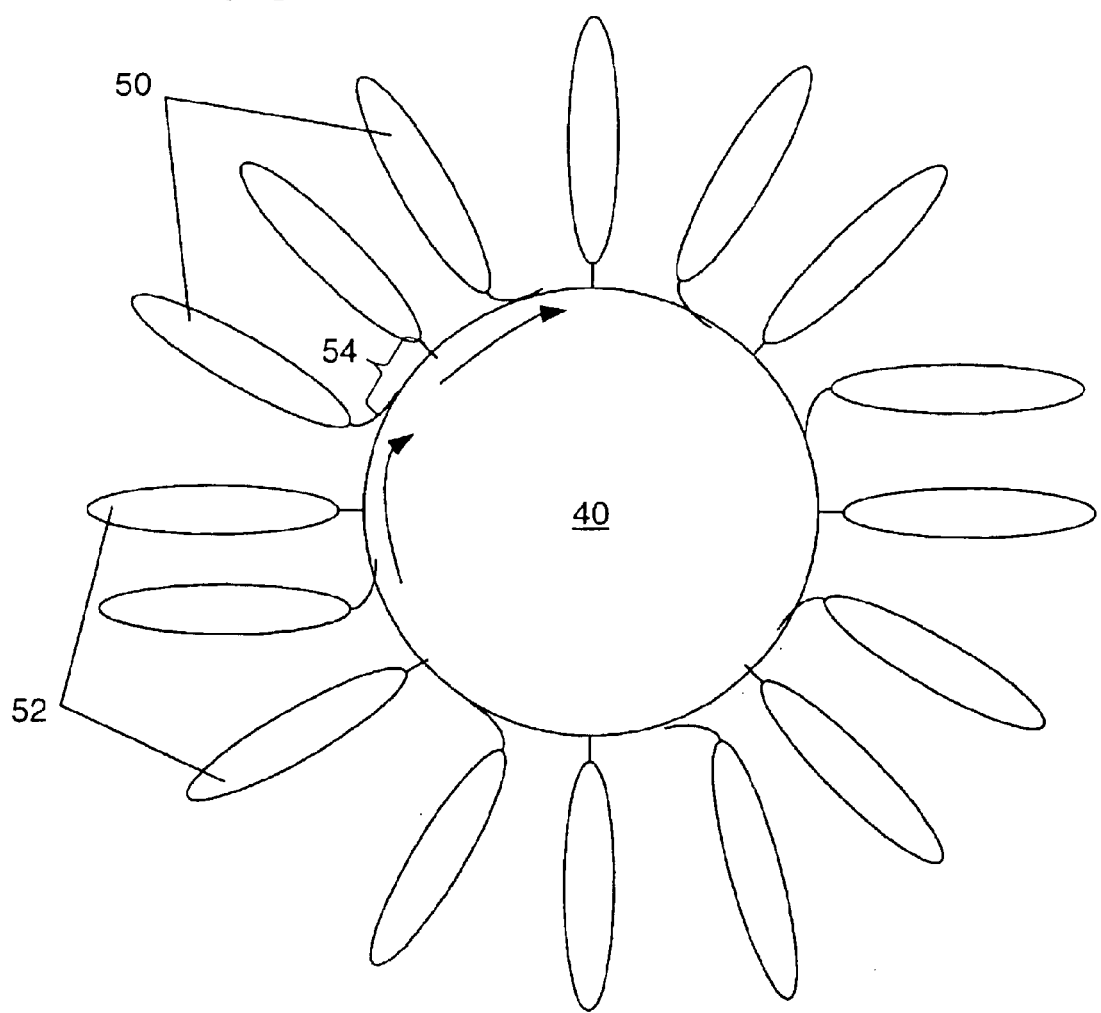
FIG. 6 is a plan view of a mixing chamber with multiple supply tubes leading thereto in alternating tangential and radial directions.

FIG. 6 depicts a plan view of one embodiment of the mixing chamber 40, having tangentially directed supply tubes 50 and radially directed supply tubes 52 connected thereto. The tangentially directed supply tubes 50 impart a swirling or helical motion to the fluid that is necessary to establish the proper residence time and mixing. The kinetic energy of the tangentially introduced fluid should be great enough relative to that of the radially introduced fluid to convert the path of the latter fluid from directly flowing toward the mixing chamber outlet (not shown) at the center of the mixing chamber 40 to a helical path. Preferably, in order to effect this motion, the kinetic energy of the tangentially flowing fluid is at least 0.5 times that of the radially flowing fluid. Therefore, it is preferable that, when the embodiment of FIG. 6 is used for the mixing of oxygen and hydrogen, the hydrogen is introduced radially and the oxygen tangentially into the mixing chamber, since the kinetic energy of the flowing oxygen will normally be substantially greater than that of the hydrogen.

The initially radially directed fluid may or may not be bent into a path as tightly wound as the tangentially directed fluid, depending on the relative kinetic energies of the two fluids. That is, the initially radially directed fluid may have as many windings along its path toward the mixing chamber outlet as the tangentially directed fluid or it may have fewer windings.

In most cases, the tangentially directed supply tubes 50 will be reserved for a first fluid and the radially directed supply tubes 52 for a second fluid. Therefore, the first fluid would be distributed, using a plurality of first fluid distribution conduits (not shown), to each of the tangentially directed supply tubes 50. Likewise, the second fluid would be distributed, using a plurality of second fluid distribution tubes (not shown), to each of the radially directed supply tubes 52. The designation of a tube as tangentially or radially directed is based on the orientation of the conduit discharge ends 54 leading into the supply chamber.

It is intended that the invention also covers the possibility of using multiple tubes for each reactant, wherein the multiple tubes for each reactant provide entry into the mixing chamber in both a substantially radial orientation and a substantially tangential orientation.

Other mixers are intended to be covered by this invention. One such mixer includes a mixing chamber wherein the mixing chamber is in fluid communication with the supply tube discharge ends of the reactants. The mixing chamber includes a porous packed bed through which the reactants are mixed. The packed bed includes, but is not limited to, inert beads, Raschig rings, slotted rings, Berl saddles, wire screens, any inert porous packing material, or combinations thereof. An alternative to the porous packed bed, includes a static mixing unit disposed within the mixing chamber. The spacing of the static mixing unit vanes is dependent on the reactants, and is sized to a dimension less than the dimension necessary to initiate ignition of the reaction.

Another alternative includes a mixing chamber in fluid communication with a plurality of the discharge ends of a first reactant supply tubes and in fluid communication with a plurality of the discharge ends of a second reactant supply tubes. The plurality of first and second discharge ends of the supply tubes are distributed in an interdigitated arrangement on the mixing chamber.

The Electrolyzer

The source of heat is from an exothermic reaction of chemicals in a well mixed gas mixture, wherein the reaction is facilitated by the presence of an appropriate catalyst. In one embodiment, the gas mixture contains hydrogen and oxygen in a substantially stoichiometric molar ratio of 2:1. The reaction of hydrogen and oxygen in the presence of the catalyst produces heat with a byproduct of water. With the stoichiometric ratio of 2:1 there is no excess gas to be removed after the reaction. To produce the gases in the stoichiometric ratio, an electrolyzer is used to decompose water to the two gases, hydrogen and oxygen. An electrolyzer converts chemical compounds into simpler compounds or elements.

In one embodiment, the present invention further includes an electrolyzer. In the instant case, the electrolyzer is used for converting water into hydrogen and oxygen. The principle is easily demonstrated by connecting platinum coated electrodes to a battery, immersing them in water in close proximity to each other, and observing the gas generated. For practical usage, the electrodes are separated to direct the different generated gases into separate receiving devices. The gases are collected, and each gas is separately directed to the mixer for mixing to form a stable mixture to be reacted upon contact with the catalyst. Each gas enters at least one inlet port to the mixer, wherein the gases are mixed and the mixture is directed to an outlet port in fluid communication with the conduit supply end.

A diagram of an electrolyzer is shown in FIG. 7. The electrolyzer 60 includes a supply reservoir 62 for supplying water to be decomposed into hydrogen and oxygen. A power source 64 provides electrical power to two electrodes 66, 68 in electrolyzer 60. The electrodes 66, 68 have different polarities, and hydrogen is generated at one electrode 66, while oxygen is generated at a second electrode 68. The hydrogen is generated as a gas and rises into a hydrogen reservoir 70. Hydrogen reservoir 70 is in fluid communication with the hydrogen supply conduits of the mixer. The oxygen is generated as a gas and rises into an oxygen reservoir 72. Oxygen reservoir 72 is in fluid communication with the oxygen supply tubes of the mixer. The gases are held at the same pressure that is controlled by the water in supply reservoir 62.

The reason for decomposing water for later reaction is that the gases have the appropriate stoichiometry for reacting the gases of oxygen and hydrogen and producing water with no other products. Water condenses rapidly in the environment at the temperatures of operation, the amount of water produced is small, and water is readily absorbed by a patient's body as it is one of the primary chemicals found in living tissue.

The volume of gases to be reacted is easily controlled by the amount of electrical power supplied to the electrolyzer. Details of an electrolyzer are well known in the art, as demonstrated in U.S. Pat. No. 6,036,827, and which is incorporated by reference. The electrical power supplied to the electrolyzer is of sufficient quantity to dissociate water at a rate between 0.01 milligrams/min. to about 10 grams/min. Optionally, a control system is incorporated in the electrolyzer to provide an upper limit on the amount of electrical power used by the electrolyzer, including, but not limited to, a fuse for shutting off power to the electrolyzer.

Another optional safety feature includes safety valves for venting excess gases generated by the electrolyzer. The valves can be preset to open when the electrolyzer generates the gases in excess of a preset limit. The safety valves can include a feedback signal to the electrolyzer, such that when the safety valves are open the electrolyzer reduces power consumption until the safety valves close.

The gases collected in the electrolyzer are collected separately in small reservoirs. The reservoirs are in fluid communication with the mixer. In one embodiment, the electrolyzer has a hydrogen reservoir and an oxygen reservoir. The hydrogen reservoir has an outlet port in fluid communication with at least one hydrogen supply tube to the mixer, and the oxygen reservoir has an outlet port in fluid communication with at least one oxygen supply tube to the mixer. The hydrogen supply tubes are made of any material that is substantially impermeable to hydrogen, and substantially inert to reacting with hydrogen. The materials chosen include, but are not limited to, those listed above for the conduit carrying the mixture of hydrogen and oxygen. The materials include tubes having a liner that is substantially impermeable to hydrogen and substantially inert to reacting with hydrogen. The oxygen reservoir is in fluid communication with the oxygen supply tubes through channels made of an appropriate material. The tubes are made of any material that is substantially impermeable to oxygen, and substantially inert to reacting with oxygen. These materials include, but are not limited to, those listed above for the conduit carrying the mixture of hydrogen and oxygen. The materials include tubes having a liner that is substantially impermeable to oxygen and substantially inert to reacting with oxygen.

In another embodiment, the hydrogen reservoir is in fluid communication with a first manifold, and the first manifold is in fluid communication with a plurality of supply tubes to the mixer. The oxygen reservoir is in fluid communication with a second manifold, and the second manifold is in fluid communication with a plurality of supply tubes to the mixer.

In an alternate embodiment, the hydrogen and oxygen reservoirs are in fluid communication with the conduit 12 directly. For the situation of a relatively long conduit 12, there is sufficient mixing through diffusion such that the gases are well mixed upon delivery to the catalyst at the delivery end of the conduit.

EXAMPLE

In an illustrative operation of the combustion needle, a gas mixture is supplied to the supply end of the conduit. The gas mixture for this illustration is composed of hydrogen and oxygen in a 2:1 molar ratio. The gas mixture travels down the conduit wherein it contacts the catalyst disposed in proximity to the delivery end of the channel. The gas reacts on contact with the catalyst and produces water and heat. The water condenses as the surrounding environment is below the boiling point of water, and the rate of reactant delivery is kept at a rate low enough to prevent the temperature rising more than about 10–15° C. above the surrounding environment. The surrounding environment is body tissue at approximately 37° C. The liquid water is forced out of the needle by the gas pressure of the reactants.

If a patient has a tumor, or tissue growth, having a 2 cm radius and 43° C. will destroy or shrink the cells in the tumor, then the thermal dose can be computed as follows. The main assumption for this example is that the thermal properties of tissue are approximately the same as water, as human tissue is approximately 70% water.

For a target tissue sample having a 2 cm radius, the volume is $1.33 * \pi * (0.02)^3 = 3.34 * 10^{-5}$ m$^3$. This gives a mass of 33.4 grams. The amount of energy to raise the target tissue to 43° C., or 6° C. above body temperature is $33.4 * 4.2 * 6 = 842$ Joules. The UHV fuel equivalent for hydrogen is $842/286000 = 2.94 * 10^{-3}$ mol $H_2$. This translates to 53 mg of water, which gives an approximate volume of 0.053 cm$^3$ of water. This would produce a tiny drop of water that is readily absorbed by the body.

The fuel supply for a 200 micrometer inner diameter channel, with a back pressure of about 6700 Pascals (50 mm Hg), or about 1 psi), arrives at the delivery end at an average velocity of 20 m/s. This translates to a volumetric flow of $20*\pi*(0.01)^2=6.27*10^{-7}$ m³/s. This translates to about 0.36 mg/s of H₂O produced which in turn equals about 5.6 watts of power delivered. The treatment time is equal to 53/0.36= 147 secs.

In other words, the hyperthermic treatment of a tumor of 2 cm in diameter is about 2.5 minutes, using a thin needle with the tip imbedded in the tumor, without exposing the patient to doses of electromagnetic radiation.

What is claimed is:

1. An apparatus for generating high intensity localized heat, comprising:
   at least one conduit defining at least one channel having a supply end and a delivery end with a connection at the supply end, and with an inner diameter of less than about 500 micrometers; and
   a catalyst disposed in proximity to the delivery end of the conduit.

2. The apparatus of claim 1 wherein the catalyst is a metal selected from the group consisting of scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), germanium (Ge), indium (In), thallium (Tl), tin (Sn), lead (Pb), antimony (Sb), bismuth (Bi), polonium (Po) and mixtures thereof.

3. The apparatus of claim 2 wherein the catalyst is a metal selected from the group consisting of platinum, palladium, rhenium, rhodium, nickel, iron, and mixtures thereof.

4. The apparatus of claim 1 wherein the channel in the conduit carries a mixture of reactants to the catalyst.

5. The apparatus of claim 1 wherein the conduit has an inner diameter of less than about 300 micrometers.

6. The apparatus of claim 1 wherein the conduit has an inner diameter of about 200 micrometers.

7. The apparatus of claim 1 wherein the conduit comprises a plurality of capillaries.

8. The apparatus of claim 1 wherein the conduit is a plurality of conduits and wherein the catalyst is disposed in proximity to the delivery end of at least one conduit.

9. The apparatus of claim 1 further comprising at least one supply tube having an inlet end and an outlet end attached to the supply end of the conduit.

10. The apparatus of claim 8 wherein the plurality of conduits is a bundle of capillaries.

11. The apparatus of claim 1 wherein the at least one conduit defines at least two channels, each channel having a supply end and a delivery end, wherein the delivery ends of the at least two channels are in proximity to each other.

12. The apparatus of claim 11 wherein a first reactant is carried in one of the channels and a second reactant is carried in another of the channels.

13. The apparatus of claim 1 further comprising a mixing unit, wherein the mixing unit comprises:
   at least one first supply tube having a first supply tube receiving end for receiving a first fluid stream and having a first supply tube discharge end opposite the first supply tube receiving end;
   at least one second supply tube having a second supply tube receiving end for receiving a second fluid stream and having a second supply tube discharge end apposite the second supply tube receiving end;
   a mixing chamber in fluid communication with the first and second supply tube discharge ends; and
   a mixing chamber outlet for discharging a mixed stream of the first and second fluid streams from the mixing chamber, the mixing chamber outlet in fluid communication with the central region of the mixing chamber, and the mixing chamber outlet in fluid communication with the supply end of the conduit.

14. The apparatus of claim 13 wherein one of the first or second supply tube discharge ends leads substantially tangentially into the mixing chamber and the other of the first and second supply tube discharge ends leads substantially radially into the mixing chamber.

15. The apparatus of claim 13 wherein the mixing chamber includes a packed porous bed.

16. The apparatus of claim 13 wherein the mixer comprises:
   a plurality of first supply tubes, each having a receiving end for receiving the first fluid stream and a first supply tube discharge end opposite the first supply tube receiving end;
   a plurality of second supply tubes, each having a receiving end for receiving a second fluid stream and a second supply tube discharge end opposite the first supply tube receiving end; and
   a mixing chamber wherein the plurality of first and second supply tube discharge ends are distributed in an interdigitated arrangement.

17. The apparatus of claim 13 for the generation of heat through a reaction, wherein the mixing chamber includes a static mixer having a dimension less than a dimension necessary to initiate ignition of the reaction.

18. The apparatus of claim 13 wherein the first and second supply tube discharge ends lead substantially radially into the mixing chamber.

19. The apparatus of claim 13 wherein the first and second supply tube discharge ends lead substantially tangentially into the mixing chamber.

20. The apparatus of claim 13 further comprising an electrolyzer for dissociating water into hydrogen and oxygen reactants having an inlet port, an oxygen outlet port and a hydrogen outlet port, wherein the oxygen and hydrogen outlet ports are each in fluid communication with individual inlet ports of the mixing unit.

21. The apparatus of claim 20 wherein the electrolysis unit is sized to dissociate water at a rate of between 0.01 mg/min and 10 grams/minute.

22. The apparatus of claim 20 further comprising a control system for controlling the rate of supply of reactants to the supply end of the conduit.

23. The apparatus of claim 22 wherein the control system controls the electrical power delivered to the electrolyzer.

24. The apparatus of claim 20 wherein the control system further comprises:
   at least one safety valve in fluid communication with at least one outlet port for venting reactants; and
   a control system for opening the safety valve.

25. The apparatus according to claim 1 wherein the delivery end of the conduit is porous.

26. The apparatus according to claim 1 wherein the channel further comprises an aperture near the delivery end of the conduit.

27. The apparatus according to claim 26 wherein the aperture is at the delivery end.

28. The apparatus according to claim 1 wherein the delivery end of the conduit includes a plurality of apertures.

29. The apparatus according to claim 28 wherein the apertures are slots.

30. The apparatus according to claim 28 wherein the apertures are elliptical pores.

31. A medical device for delivering intense heat to a localized region, the device comprising:
- a conduit defining a channel and having an inlet port and an outlet port;
- a catalyst disposed in close proximity to the outlet port of the conduit;
- a mixer for mixing reactants, the mixer having a plurality of inlet ports and an outlet port, wherein the reactants enter through the inlet ports and a mixture exits the outlet port, wherein the outlet port is in fluid communication with the conduit inlet port; and
- an electrolysis device for producing the reactants and directing the reactants to the inlet ports of the mixer.

32. The device of claim 31 wherein the conduit is made of a flexible material.

33. The device of claim 31 wherein the conduit is made from a material selected from the group consisting of stainless steels, inconels, ceramics, and plastics.

34. The device of claim 33 wherein the conduit is coated with an impermeable material that is inert to the reactants oxygen and hydrogen.

35. The device of claim 34 wherein the conduit is coated with a fluorinated hydrocarbon polymer.

36. The device of claim 31 wherein the catalyst is selected from the group consisting of platinum, palladium, rhenium, rhodium, nickel, iron, and mixtures thereof.

37. An apparatus for generating a high intensity localized heat comprising:
- a well having an open end and a closed end;
- a conduit inserted in the well, having a supply end and a delivery end wherein the delivery end is in proximity to the closed end of the well; and
- a catalyst disposed in proximity to the delivery end of the conduit.

38. The apparatus of claim 37 wherein the catalyst is a metal selected form the group consisting of scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), mercy (Hg), and mixtures thereof.

39. The apparatus of claim 37 wherein the conduit has an inner diameter of less than about 500 micrometers.

40. The apparatus of claim 37 wherein the conduit comprises a plurality of conduits, wherein each conduit has an inner diameter of less than about 400 micrometers.

41. A process of applying heat for hyperthermic treatment of tissue, comprising the steps of:
- injecting a needle into the tissue, wherein the needle defines a channel and has a supply end and a delivery end, and has a catalyst disposed in proximity to the delivery end; and
- supplying gaseous reactants to the catalyst through the supply end of the needle;
- and reacting the reactants over the catalyst thereby generating high intensity heat.

42. The process of claim 41 further comprising the step of generating the gaseous reactants from an electrolyzer.

43. The process of claim 42 further comprising the step of controlling the rate of generating the gaseous reactants by controlling the rate of usage of electrical power thereby delivering a measured dose of heat to the tissue.

44. The process of claim 41 further comprising the step of supplying the gaseous reactants from separate reactant sources.

45. The process of claim 41 further comprising the step of feeding the gaseous reactants in a mixer to form a mixture prior to supplying the gaseous reactants to the catalyst.

46. The process of claim 45 further comprising the step of feeding the mixture from the mixer to the supply end of the needle.

47. The process of claim 45 further comprising the step of controlling the ratio of gaseous reactants fed to the mixer.

48. The process of claim 41 further comprising the step of locating the delivery end of the needle with a thermal sensor.

49. The process of claim 41 further comprising the step of moving the delivery end of the needle relative to the tissue to deliver a dose of heat along a line.

50. A process of applying heat for hyperthermic treatment of tissue, comprising the steps of:
- injecting a needle into the tissue, wherein the needle defines a channel and has a supply end and a delivery end, and has a catalyst disposed in proximity to the delivery end;
- passing gaseous reactants from an electrolyzer to a mixer to form a mixture;
- feeding the mixture from the mixer to the supply end of the needle; and
- flowing the mixture over the catalyst disposed at the delivery end of the needle thereby reacting the mixture and generating heat.

* * * * *